(12) United States Patent
Wei et al.

(10) Patent No.: US 11,344,193 B2
(45) Date of Patent: May 31, 2022

(54) METHOD FOR PERFORMING AN ASSESSMENT OF VISION

(71) Applicant: Chang Gung University, Taoyuan (TW)

(72) Inventors: Jyh-Da Wei, Taoyuan (TW); Jerry Chien-Chieh Huang, Taoyuan (TW); Shin-Yi Chen, Taoyuan (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 242 days.

(21) Appl. No.: 16/440,173

(22) Filed: Jun. 13, 2019

(65) Prior Publication Data

US 2019/0380572 A1   Dec. 19, 2019

(30) Foreign Application Priority Data

Jun. 15, 2018 (TW) ................................ 107120723

(51) Int. Cl.
*A61B 3/032* (2006.01)
*G06F 3/0482* (2013.01)
(Continued)

(52) U.S. Cl.
CPC ............ *A61B 3/032* (2013.01); *A61B 3/0058* (2013.01); *G06F 3/0482* (2013.01); *G06T 13/80* (2013.01); *G16H 10/20* (2018.01)

(58) Field of Classification Search
CPC ......... A61B 3/032; A61B 3/0058; A61B 3/02; G06T 13/80; G06F 3/0482; G16H 10/20; G16H 50/20
See application file for complete search history.

(56) References Cited

U.S. PATENT DOCUMENTS 5,680,531 A * 10/1997 Litwinowicz ........... G06T 13/80
                                                                345/473
6,386,707 B1 * 5/2002 Pellicano ................. A61B 3/18
                                                                351/246
(Continued)

FOREIGN PATENT DOCUMENTS

CN     102686146 A  *  9/2012  ............. A61B 3/022
CN     109152559 A  *  1/2019  ............. A61B 5/4076
EP       3329837 A1  *  6/2018  ............. A61B 3/032

OTHER PUBLICATIONS

Wilkinson et al. Detection and recognition of radial frequency patterns. Vision Research vol. 38, Issue 22, Nov. 1998, pp. 3555-3568. (Year: 1998).*

(Continued)

*Primary Examiner* — Amy M Levy
(74) *Attorney, Agent, or Firm* — Osha Bergman Watanabe & Burton LLP

(57) ABSTRACT

A method for performing an assessment of vision is provided, and comprises: determining a current difficulty level for the assessment; displaying a question of the assessment, the question including a visual element that has a movable pattern, the movable pattern having at least one variable attribute that is related to the current difficulty level; in response to receipt of an inputted answer, determining whether the inputted answer is correct; and determining whether the assessment is to be concluded, and in the affirmative, generating a result of the assessment based on the current difficulty level.

11 Claims, 12 Drawing Sheets

(51) Int. Cl.
*G16H 10/20* (2018.01)
*A61B 3/00* (2006.01)
*G06T 13/80* (2011.01)

(56) References Cited

U.S. PATENT DOCUMENTS

| | | | | |
|---|---|---|---|---|
| 10,398,304 B2* | 9/2019 | Lee | ......... | A61B 3/036 |
| 2005/0225720 A1* | 10/2005 | Ridings | ......... | A61B 3/032 |
| | | | | 351/200 |
| 2006/0152675 A1* | 7/2006 | Toshima | ......... | A61B 3/032 |
| | | | | 351/205 |
| 2007/0166675 A1* | 7/2007 | Atkins | ......... | G09B 7/00 |
| | | | | 434/236 |
| 2010/0253905 A1* | 10/2010 | Lawton | ......... | G09B 19/00 |
| | | | | 351/203 |
| 2011/0027766 A1* | 2/2011 | Yoo | ......... | A61B 3/032 |
| | | | | 434/262 |
| 2011/0037950 A1* | 2/2011 | Hytowitz | ......... | A61B 3/032 |
| | | | | 351/239 |
| 2011/0255055 A1* | 10/2011 | Spaeth | ......... | A61B 3/032 |
| | | | | 351/239 |
| 2013/0176534 A1* | 7/2013 | Frankfort | ......... | A61B 3/113 |
| | | | | 351/209 |
| 2014/0285769 A1* | 9/2014 | Palanker | ......... | A61B 3/032 |
| | | | | 351/223 |
| 2015/0150444 A1* | 6/2015 | Bex | ......... | A61B 3/022 |
| | | | | 351/242 |
| 2016/0095513 A1* | 4/2016 | Shapiro | ......... | G02F 1/0123 |
| | | | | 351/209 |
| 2016/0213243 A1* | 7/2016 | Palanker | ......... | G16H 80/00 |
| 2018/0008142 A1* | 1/2018 | Garoon | ......... | A61B 3/0025 |
| 2019/0183330 A1* | 6/2019 | Schiffman | ......... | G06F 3/0482 |
| 2019/0298165 A1* | 10/2019 | Greivenkamp, Jr. | ......... | |
| | | | | A61B 3/0033 |

OTHER PUBLICATIONS

Levitt, Transformed Up-Down Methods in Psychoacoustics. Doctoral Program in Speech The City University of New York Graduate Center, New York. (1970). 11 pages. (Year: 1970).*

Mayer et al. Preferential looking acuity obtained with a staircase procedure in pediatric patients. Invest. Ophthalmol. Vis. Sci. Oct. 1982. pp. 538-543. (Year: 1982).*

Ginsburg. "Contrast Sensitivity, Drivers' Visibility, and Vision Standards", published 1987. (Year: 1987).*

* cited by examiner

EШΠE∃Ш∃   EШΠE∃Ш∃

Please keep a distance throughout the assessment at which the characters on the upper left side can be identified clearly while the characters on the upper right side cannot be identified clearly Confirm

FIG. 3

METHOD FOR PERFORMING AN ASSESSMENT OF VISION

CROSS-REFERENCE TO RELATED APPLICATION

This application claims priority of Taiwanese Patent Application No. 107120723, filed on Jun. 15, 2018.

FIELD

The disclosure relates to a method of performing an assessment of vision.

BACKGROUND

Conventionally, an assessment of vision may be performed using a number of ways or using specifically configured devices or systems. For example, visual acuity of a person may be assessed using a variety of eye charts, such as a Landolt C chart, a Snellen chart, etc. A contrast sensitivity chart may be used to determine whether a person has dry eye syndrome. A flicker fusion system and Heuer's 10-point scale questionnaire may be used to detect eye strain or visual fatigue of a person.

SUMMARY

One object of the disclosure is to provide a method for performing a performing an assessment of vision.

According to one embodiment of the disclosure, the method is implemented using an electronic device that includes a processor, an input unit and a display unit. The method includes:

a) determining, by the processor, a current level of difficulty for the assessment of vision;

b) controlling, by the processor, the display unit to display a question of the assessment of vision, the question including a visual element that has a movable pattern, the movable pattern having at least one variable attribute that is related to the current level of difficulty;

c) in response to receipt of an inputted answer via the input unit, determining, by the processor, whether the inputted answer is correct;

d) determining, by the processor, based on the determination of step c), whether the assessment of vision is to be concluded;

e) when it is determined that the assessment of vision is to be concluded, generating, by the processor, a result of the assessment of vision based on the current level of difficulty.

BRIEF DESCRIPTION OF THE DRAWINGS

Other features and advantages of the disclosure will become apparent in the following detailed description of the embodiments with reference to the accompanying drawings, of which:

FIG. 3 illustrates an instruction screen for instructing the user to keep a suitable distance during the assessment of vision;

DETAILED DESCRIPTION

Figure 1:
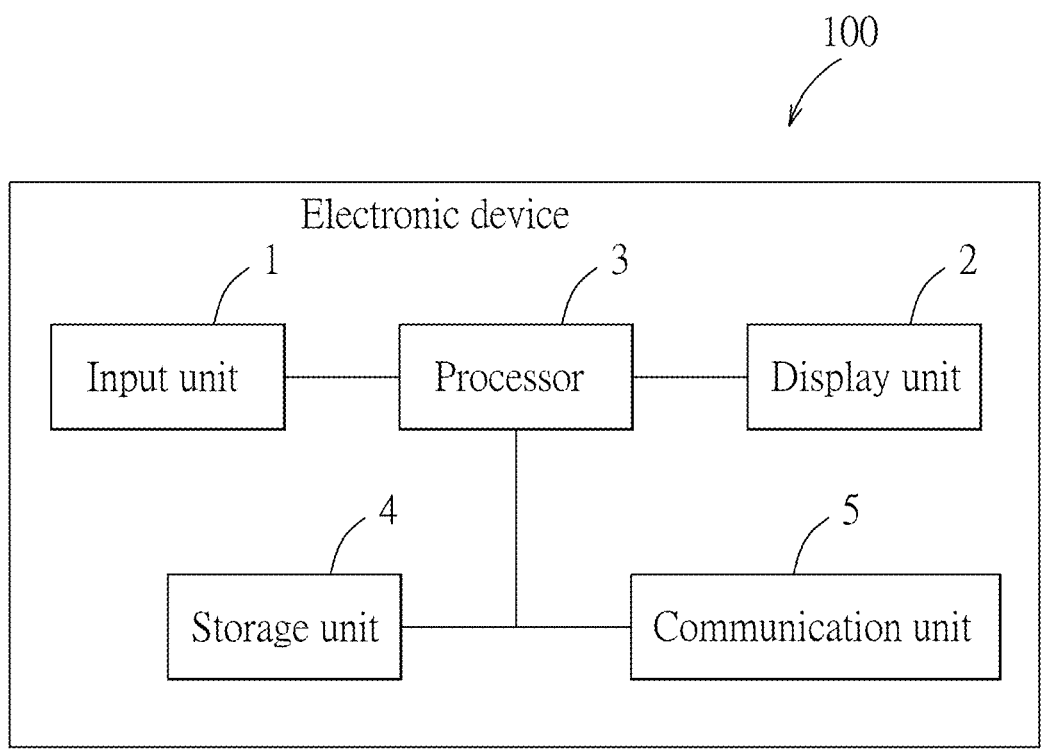
FIG. 1 is a block diagram illustrating an electronic device according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

FIG. 1 is a block diagram illustrating an electronic device 100 according to one embodiment of the disclosure. In this embodiment, the electronic device 100 may be embodied using one of a smartphone, a personal computer, a desktop computer, a laptop, a tablet, etc.

The electronic device 100 includes an input unit 1, a display unit 2, a processor 3, a storage unit 4 and a communication unit 5.

The input unit 1 serves as a user interface for enabling a user to interact with the electronic device 100. In some embodiments, the input unit 1 may be embodied using a keyboard and a mouse (not shown in the drawings). In the case that the electronic device 100 is embodied using one of a smartphone or a tablet, the input unit 1 may be integrated with the display unit 2 in the form of a touchscreen.

The processor 3 may include, but not limited to, a single core processor, a multi-core processor, a dual-core mobile processor, microprocessor, a microcontroller, a digital signal processor (DSP), a field-programmable gate array (FPGA), an application specific integrated circuit (ASIC), and/or a radio-frequency integrated circuit (RFIC), etc.

The storage unit 4 may be embodied using one or more of a hard disk, a solid-state drive (SSD), flash memory, and other non-transitory storage medium. In this embodiment, the storage unit 4 stores an application program that is associated with a method for performing an assessment of vision for a user.

The communication unit 5 may include a short-range wireless communication module supporting a short-range wireless communication network using a wireless technology of Bluetooth® and/or Wi-Fi, etc., and a mobile communication module supporting telecommunication using Long-Term Evolution (LTE), the third generation (3G) and/or fourth generation (4G) of wireless mobile telecommunications technology, and/or the like.

Figure 2:
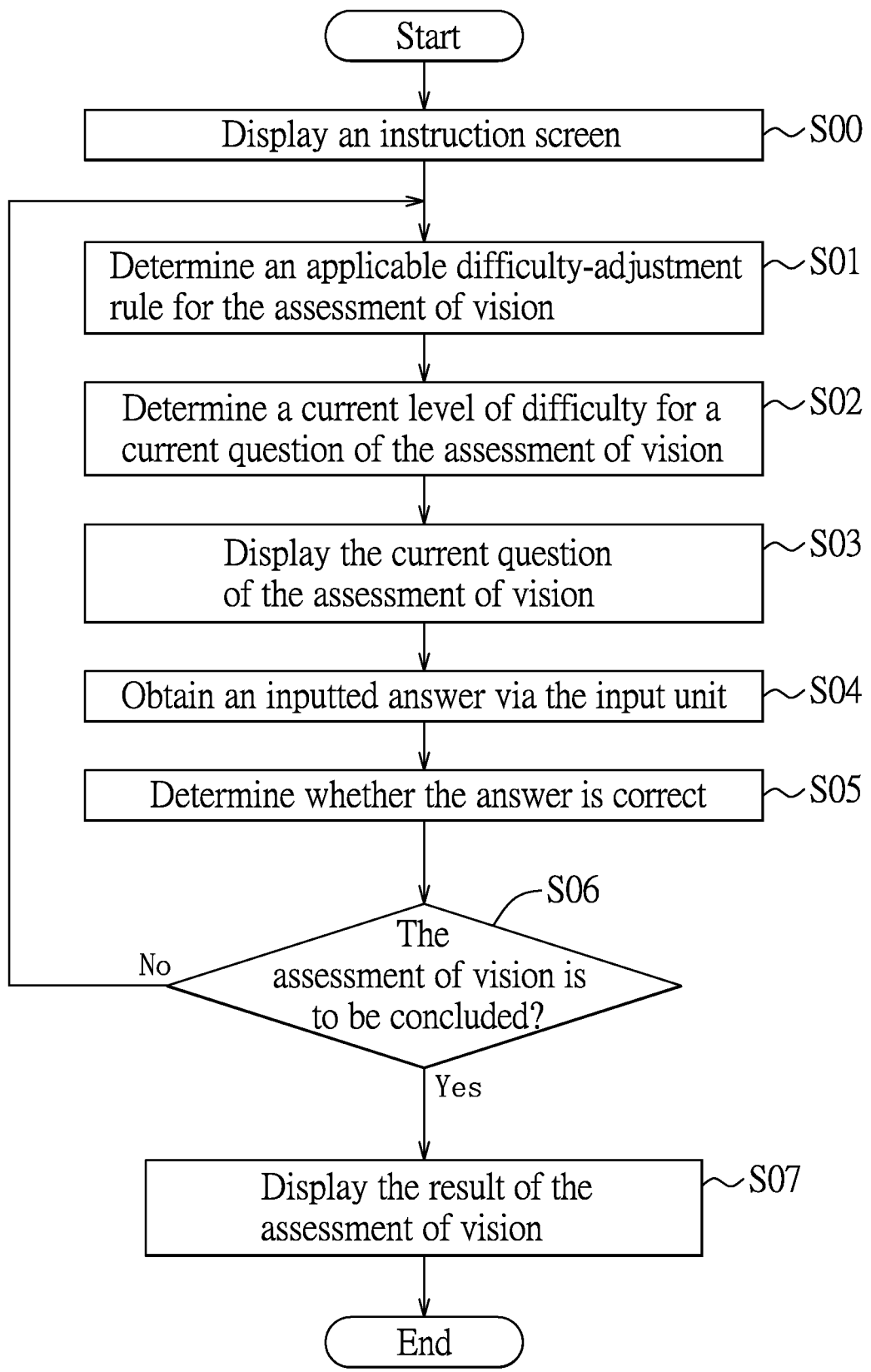
FIG. 2 is a flow chart illustrating steps of a method for performing an assessment of vision for a user according to one embodiment of the disclosure.

FIG. 2 is a flow chart illustrating steps of the method for performing an assessment of vision for a user according to one embodiment of the disclosure. In this embodiment, the method is performed by the electronic device 100 of FIG. 1, and may be initiated by the user operating the electronic device 100 to execute the application program stored in the storage unit 4. When executing the application program, the processor 3 is configured to perform steps as shown in FIG. 2 and described in the following paragraphs.

In step S00, the processor 3 controls the display unit 2 to display an instruction screen for instructing the user to keep his/her eyes at a suitable distance away from the display unit 2.

For example, as shown in FIG. 3, the instruction screen may include two sets of symbols, one of which is larger in size than the other. Additionally, the instruction screen may further include texts instructing the user to keep his/her eyes at the suitable distance away from the display unit 2, where he/she is able to identify the left one of the two sets of symbols (i.e., the one that is larger in size) clearly, while unable to identify the right one of the two sets of symbols (i.e., the one that is smaller in size) clearly.

After the user determines that his/her eyes are at the suitable distance away from the display unit 2, the user may operate the input unit 1 to input a confirmation command (e.g., tapping on a confirm button shown on the display unit 2). In response to receipt of the confirmation command, the flow proceeds to step S01.

In step S01, the processor 3 determines an applicable difficulty-adjustment rule for the assessment of vision. The applicable difficulty-adjustment rule is used for adjusting a level of difficulty of a question of the assessment of vision.

Figure 4:
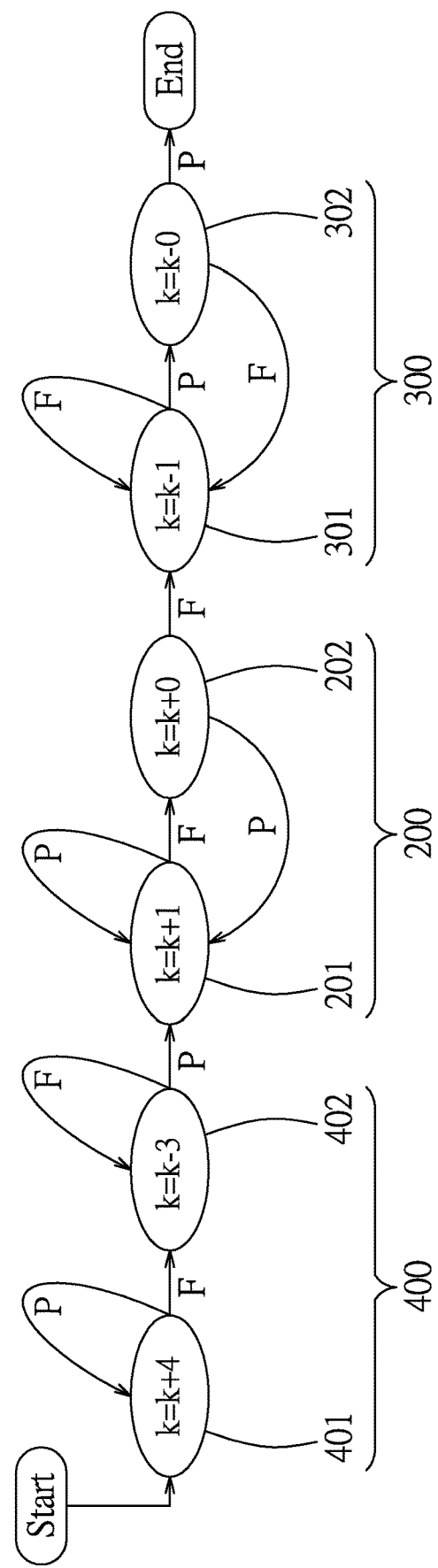
FIG. 4 is a schematic diagram illustrating an algorithm for adjusting a level of difficulty during the assessment of vision.

Specifically, as shown in FIG. 4, the applicable difficulty-adjustment rule may be selected from one of a first difficulty-adjustment rule 201, a second difficulty-adjustment rule 202, a third difficulty-adjustment rule 301, a fourth difficulty-adjustment rule 302, a fifth difficulty-adjustment rule 401, and a sixth difficulty-adjustment rule 402. The first difficulty-adjustment rule 201 and the second difficulty-adjustment rule 202 belong to a level-up group 200. The third difficulty-adjustment rule 301 and the fourth difficulty-adjustment rule 302 belong to a level-down group 300. The fifth difficulty-adjustment rule 401 and the sixth difficulty-adjustment rule 402 belong to a rapid-change group 400.

It is noted that right after the method is initiated (that is to say, when the applicable difficulty-adjustment rule is to be decided by the processor 3 for the first time), the processor 3 may take a default difficulty-adjustment rule as the applicable difficulty-adjustment rule. For example, the processor 3 may make the fifth difficulty-adjustment rule 401 of the rapid-change group 400 the default difficulty-adjustment rule (to serve as the very first, initial applicable difficulty-adjustment rule). Afterward, when the flow goes back to this step again, the applicable difficulty-adjustment rule may be re-determined according to an algorithm for adjusting the level of difficulty (see FIG. 4) based on the user's answer to a question of the assessment of vision, and details thereof will be described in later paragraphs.

In step S02, the processor 3 determines a current level of difficulty (k) for a current question of the assessment of vision. It is noted that right after the method is initiated (that is to say, when the current level of difficulty (k) is to be decided for the first time), the processor 3 may set the current level of difficulty (k) to a default level (e.g., k=3). Afterward, when the flow goes back to this step again, the current level of difficulty (k) may be adjusted according to the applicable difficulty-adjustment rule that is re-determined in step S01.

In this embodiment, as shown in FIG. 4, when step S02 is implemented for the second time or onwards, and when the applicable difficulty-adjustment rule is the first difficulty-adjustment rule 201, the processor 3 adjusts the current level of difficulty (k) by adding a first increment number (e.g., k=k+1). When the applicable difficulty-adjustment rule is the second difficulty-adjustment rule 202, the processor 3 keeps the current level of difficulty (k) unchanged (i.e., k=k+0). When the applicable difficulty-adjustment rule is the third difficulty-adjustment rule 301, the processor 3 adjusts the current level of difficulty (k) by subtracting a first decrement number (e.g., k=k−1). When the applicable difficulty-adjustment rule is the fourth difficulty-adjustment rule 302, the processor 3 keeps the current level of difficulty (k) unchanged (i.e., k=k−0). When the applicable difficulty-adjustment rule is the fifth difficulty-adjustment rule 401, the processor 3 adjusts the current level of difficulty (k) by adding a second increment number that is larger than the first increment number (e.g., k=k+4). When the applicable difficulty-adjustment rule is the sixth difficulty-adjustment rule 402, the processor 3 adjusts the current level of difficulty (k) by subtracting a second decrement number that is larger than the first decrement number (e.g., k=k−3).

Figure 5:
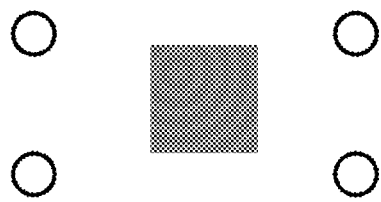
FIG. 5 illustrates a question of the assessment of vision displayed to the user.

In step S03, the processor 3 controls the display unit 2 to display the current question of the assessment of vision. It should be understood that the assessment of vision may include a plurality of questions. The current question displayed on the display unit 2 includes an instruction to answer the current question, and a visual element having a movable pattern that is associated with the current level of difficulty (k). The movable pattern has at least one variable attribute that is related to the current level of difficulty (k). In one example as shown in FIG. 5, one question is displayed. The visual element is an animated image (e.g., GIF file) showing movement of a movable pattern (e.g., a wave pattern such as a ripple pattern). Additionally, the visual element is generated to present an animated sequence such that the ripple pattern is perceived by the user as "being in motion".

Figure 6:
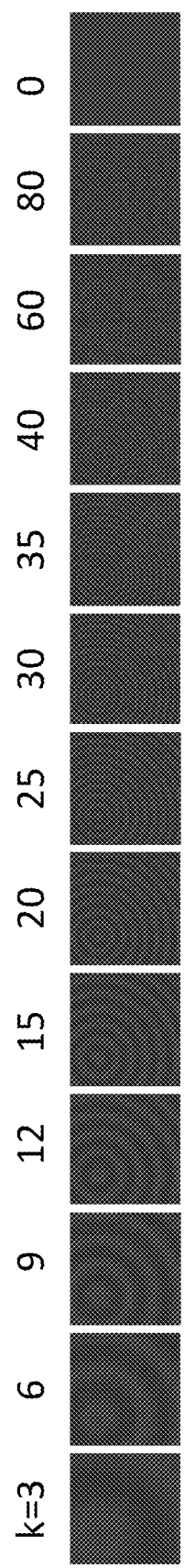
FIG. 6 illustrates how a visual element varies based on different levels of difficulty.

The movable pattern (ripple pattern) has a wavelength that is negatively related to the current level of difficulty (k). As shown in FIG. 6, as the current level of difficulty (k) increases, the wavelength of the ripple pattern decreases, making the ripple pattern increasingly difficult for the user to see clearly.

In generating the visual element with N*N pixels, the processor 3 may employ the following equation for each pixel at one of T number of time points that are evenly distributed in a specific period of movement of the ripple pattern:

$$R2(i, j, p, q, t) = B + \left[ A \cdot \sin\left( \frac{\pi k}{N} \sqrt{(i-p)^2 + (j-q)^2} - \frac{2\pi}{T} t \right) \right],$$

where $(i,j) \in \{0, 1, \ldots, N-1\}^2$ represents a location of the pixel of the visual element, $(p,q) \in \{0, 1, \ldots, N-1\}^2$ represents a location of a center of the ripple pattern, $t \in \{0, 1, \ldots, T-1\}$ represents said one of the T number of time points, B represents an average brightness (between 0 and 255), A represents a maximum amplitude (between 0 and min (B, 255-B)), and R2 represents pixel value of the pixel located at (i,j).

In other embodiments, the visual element may be in other forms such as a Graphics Interchange Format (GIF) file, a video file, etc.

The instruction to answer the current question provides directions on how a user is to answer the displayed question. For example, in the example of FIG. 5, the user is directed to point out a relative location of a center of the ripple pattern (by clicking on one of four radio buttons surrounding the visual element). When the user cannot see the ripple pattern clearly, the user may choose to click on a fifth radio button indicating "Not sure". After selecting and clicking one of the radio buttons, the user is directed to click a "Next question" button.

In step S04, the processor 3 obtains an inputted answer via the input unit 1. The inputted answer is inputted by the user using the input unit 1 to click one of the radio buttons, and is transmitted from the input unit 1 to the processor 3 when the user clicks the "Next question" button.

In step S05, in response to receipt of the inputted answer, the processor 3 determines whether the inputted answer is correct. It is noted that when the inputted answer indicates that the user selected "Not sure", the processor 3 deems the inputted answer incorrect.

In step S06, the processor 3 determines whether the assessment of vision is to be concluded. Specifically, the processor 3 determines whether a concluding condition has been met based on at least the determination of step S05.

When it is determined that the assessment of vision is to be concluded, the flow proceeds to step S07, in which the processor 3 generates a result of the assessment of vision based on the current level of difficulty (k), and controls the display unit 2 to display the result of the assessment of vision (for example, the result displayed may include the current level of difficulty (k) at the conclusion of the assessment). Otherwise, the flow goes back to step S01.

At this stage, when the flow goes to step S01, the processor 3 determines how to update the applicable difficulty-adjustment rule based on the inputted answer and the applicable difficulty-adjustment rule.

Specifically, as shown in FIG. 4, when the applicable difficulty-adjustment rule is the first difficulty-adjustment rule 201 and it is determined in step S05 that the inputted answer is correct (labeled using the character "P"), the processor 3 maintains the applicable difficulty-adjustment rule as the first difficulty-adjustment rule 201.

When the applicable difficulty-adjustment rule is the first difficulty-adjustment rule 201 and it is determined in step S05 that the inputted answer is incorrect (labeled using the character "F"), the processor 3 switches the applicable difficulty-adjustment rule to the second difficulty-adjustment rule 202.

When the applicable difficulty-adjustment rule is the second difficulty-adjustment rule 202 and it is determined in step S05 that the inputted answer is correct, the processor 3 switches the applicable difficulty-adjustment rule to the first difficulty-adjustment rule 201.

When the applicable difficulty-adjustment rule is the second difficulty-adjustment rule 202 and it is determined in step S05 that the inputted answer is incorrect, the processor 3 switches the applicable difficulty-adjustment rule to the third difficulty-adjustment rule 301.

When the applicable difficulty-adjustment rule is the third difficulty-adjustment rule 301 and it is determined in step S05 that the inputted answer is incorrect, the processor 3 maintains the applicable difficulty-adjustment rule as the third difficulty-adjustment rule 301.

When the applicable difficulty adjustment rule is the third difficulty-adjustment rule 301 and it is determined in step S05 that the inputted answer is correct, the processor 3 switches the applicable difficulty-adjustment rule to the fourth difficulty-adjustment rule 302.

When the applicable difficulty-adjustment rule is the fourth difficulty-adjustment rule 302 and it is determined in step S05 that the inputted answer is incorrect, the processor 3 switches the applicable difficulty-adjustment rule to the third difficulty-adjustment rule 301.

When the applicable difficulty-adjustment rule is the fifth difficulty-adjustment rule 401 and it is determined in step S05 that the inputted answer is correct, the processor 3 maintains the applicable difficulty-adjustment rule as the fifth difficulty-adjustment rule 401.

When the applicable difficulty-adjustment rule is the fifth difficulty-adjustment rule 401 and it is determined in step S05 that the inputted answer is incorrect, the processor 3 switches the applicable difficulty-adjustment rule to the sixth difficulty-adjustment rule 402.

When the applicable difficulty-adjustment rule is the sixth difficulty-adjustment rule 402 and it is determined in step S05 that the inputted answer is correct, the processor 3 switches the applicable difficulty-adjustment rule to the first difficulty-adjustment rule 201.

When the applicable difficulty-adjustment rule is the sixth difficulty-adjustment rule 402 and it is determined in step S05 that the inputted answer is incorrect, the processor 3 maintains the applicable difficulty-adjustment rule as the sixth difficulty-adjustment rule 402.

It is noted that in this embodiment, in step S06, the processor 3 determines that the assessment of vision is to be concluded when the applicable difficulty-adjustment rule is the fourth difficulty-adjustment rule 302 and it is determined in step S05 that the inputted answer is correct.

As such, after determining the current level of difficulty (k), the processor 3 controls the display unit 2 to display another question for the assessment of vision based on the current level of difficulty (k). The assessment of vision may then continue until the conclude condition is met.

Figure 7:
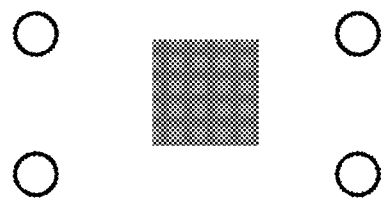
FIG. 7 illustrates another kind of question to be displayed during the assessment of vision, according to one embodiment of the disclosure.

FIG. 7 illustrates another kind of question to be displayed by the display unit 2 during the assessment of vision, according to one embodiment of the disclosure.

Specifically, in this embodiment, the visual element of the question is an animated image having a movable pattern (i.e., a movable grid pattern). The movable grid pattern may be formed using waves, that is to say, the movable grid pattern may be referred to as a wave-based movable grid pattern. In one example, the movable grid pattern is formed by two sets of component waves extending in non-parallel directions. Additionally, the visual element is generated to present an animated sequence, such that the movable grid pattern is perceived by the user of as "moving".

In the example of FIG. 7, for the instruction to answer the question, the user is directed to point out a moving direction of the movable grid pattern (by clicking on one of four radio buttons around the visual element). When the user cannot see the movable grid pattern clearly, the user may choose to click on a fifth radio button indicating "Not sure".

Figure 8:
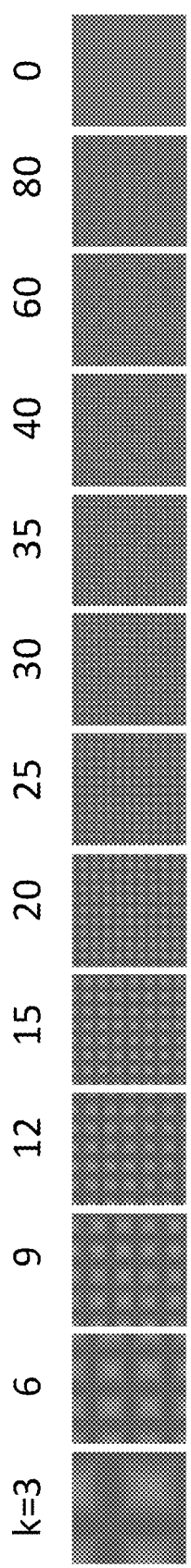
FIG. 8 illustrates how another visual element varies based on different levels of difficulty.

Specifically, the wave-based movable grid pattern has a grid size (or a grid width) according to the wave lengths of the component waves. The grid size is negatively related to the level of difficulty (k). As shown in FIG. 8, as the current level of difficulty (k) increases, the grid size of the movable grid pattern becomes smaller, making it harder for the user to see clearly.

In generating the visual element with N*N pixels, the processor 3 may employ the following equation for each pixel at one of T number of time points that are evenly distributed in a specific period of movement of the movable grid pattern:

$$G2(i, j, p, q, t) =$$
$$B + \left[A \cdot \min\left(\cos\left(\frac{(2\pi+1)k}{2N}i + \frac{2\pi}{T}p \cdot t\right), \cos\left(\frac{(2\pi+1)k}{2N}j + \frac{2\pi}{T}q \cdot t\right)\right)\right],$$

where $(i,j) \in \{0, 1, \ldots, N-1\}^2$ represents a location of the pixel of the visual element, $(p,q) \in \{-1, 0, 1\}^2$ represents a moving direction of the movable grid pattern, $t \in \{0, 1, \ldots, T-1\}$ represents said one of the T number of time points, B represents an average brightness (between 0 and 255), A represents a maximum amplitude (between 0 and min(B, 255-B)), and G2 represents pixel value of the pixel located at (i,j).

Figure 9:
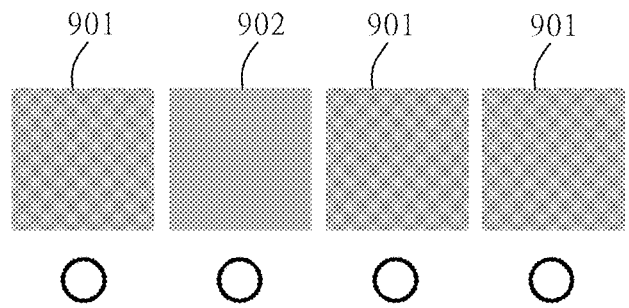
FIG. 9 illustrates yet another kind of question to be displayed during the assessment of vision, according to one embodiment of the disclosure.

FIG. 9 illustrates yet another kind of question to be displayed by the display unit 2 during the assessment of vision, according to one embodiment of the disclosure.

In this embodiment, the question includes a plurality of visual elements (three visual elements 901 are present in FIG. 9), a reference image (labeled 902 in FIG. 9) and an instruction to answer the question by identifying the reference image 902. For example, each of the visual elements 901 may be an animated image having a movable pattern (e.g., a movable rhombus-shaped pattern) and generated to "move" in a manner similar to the visual element shown in FIG. 7, and the reference image 902 does not include a movable pattern. The reference image 902 may be one pre-stored in the storage unit 4, or generated in a manner similar to that for generating the visual elements 901.

Figure 10:
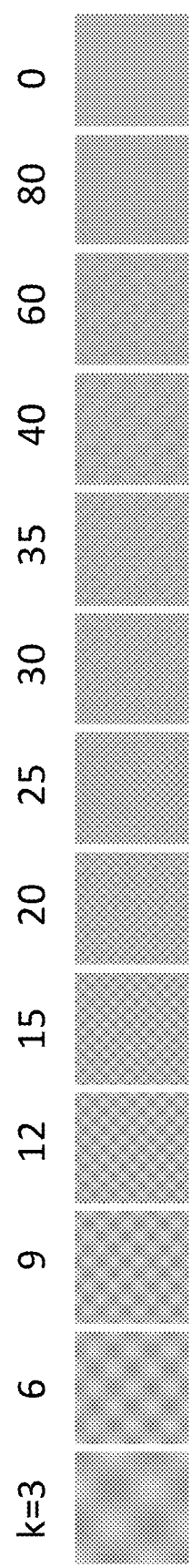
FIG. 10 illustrates how yet another visual element varies based on different levels of difficulty.

The movable rhombus-shaped pattern has a grid size that is negatively related to the current level of difficulty (k). As shown in FIG. 10, as the current level of difficulty (k) increases, the grid size of the movable rhombus-shaped pattern becomes smaller, making it harder for the user to see clearly and therefore harder for the user to distinguish the reference image 902 from the visual elements 901.

In generating the visual element with W*N pixels, the processor 3 may employ the following equation for each pixel at one of T number of time points that are evenly distributed in a specific period of movement of the movable rhombus-shaped pattern:

$$D2(i, j, p, q, t) =$$
$$B + \left[A \cdot \cos\left(\frac{(2\pi+1)k}{2N}i + \frac{2\pi}{T}p \cdot t\right)\cos\left(\frac{(2\pi+1)k}{2N}j + \frac{2\pi}{T}q \cdot t\right)\right],$$

where $(i,j) \in \{0, 1, \ldots, N-1\}^2$ represents a location of the pixel of the visual element, $(p,q) \in (-1, 0, 1)^2$ represents a moving direction of the movable rhombus-shaped pattern, $t \in \{0, 1, \ldots, T-1\}$ represents said one of the T number of time points, B represents an average brightness (between 0 and 255), A represents a maximum amplitude (between 0 and min (B, 255-B)), and D2 represents pixel value of the pixel located at (i,j).

In one example, the reference image includes a movable rhombus-shaped pattern, and the movable rhombus-shaped pattern of the reference image has at least one variable attribute that is related to a reference level of difficulty, and the reference level of difficulty is made to be different from the current level of difficulty (k). For example, the variable attribute may be selected from one of a moving direction of the movable rhombus-shaped pattern, an amplitude of the movable rhombus-shaped pattern, a grid size of the movable rhombus-shaped pattern, a moving speed of the movable rhombus-shaped pattern. The reference level of difficulty may be a relatively large number such as 80. By applying a different value to one or more parameters, the reference image may be generated using the above equation used for generating the visual elements.

Figure 11:
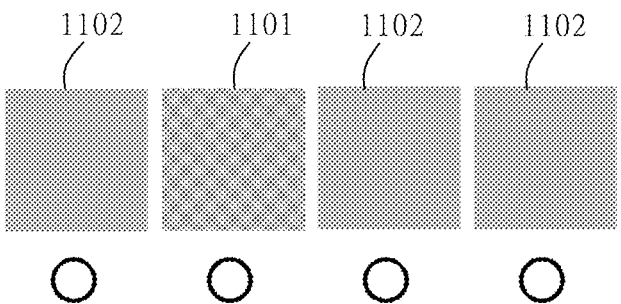
FIGS. 11 and 12 illustrate additional kinds of question to be displayed during the assessment of vision, according to some embodiments of the disclosure.

FIG. 11 illustrates one kind of question to be displayed by the display unit 2 during the assessment of vision, according to one embodiment of the disclosure.

In this embodiment, the question includes one visual element (labeled 1101 in FIG. 11), a plurality of reference images (three reference images 1102 are present in FIG. 11), and an instruction to answer the question by identifying the visual element 1101.

For example, the visual element 1101 may be an animated image having a movable pattern (e.g., a movable rhombus-shaped pattern) and generated to "move" in a manner similar to the visual element shown in FIG. 7, whereas the reference images 1102 do not include a movable rhombus-shaped pattern and may be identical to one another.

In one example, each of the reference images 1102 includes a movable pattern, and the movable pattern of each of the reference images has at least one variable attribute that is related to a reference level of difficulty, and the reference level of difficulty is made to be different from the current level of difficulty (k).

For example, the variable attribute may be selected from one of a moving direction of the movable pattern, an amplitude of the movable pattern, a grid size of the movable pattern, and a moving speed of the movable pattern. The reference level of difficulty may be a relatively large number such as 80. By applying a different value to one or more parameters, the reference images may be generated using the above equation used for generating the visual element.

Figure 12:
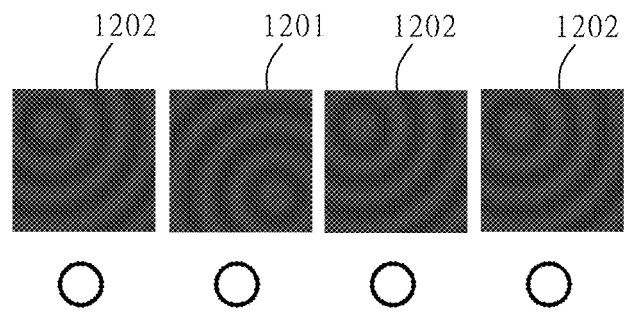

FIG. 12 illustrates one kind of question to be displayed by the display unit 2 during the assessment of vision, according to one embodiment of the disclosure.

In this embodiment, the question includes one visual element (labeled 1201 in FIG. 12), a plurality of reference images (three reference images 1202 are present in FIG. 12), and an instruction to answer the question by identifying the visual element 1201.

In this embodiment, each of the visual element 1201 and the reference images 1202 includes a movable pattern (e.g., a ripple pattern), and the movable pattern of each of the visual element 1201 and the reference images 1202 has at least one variable attribute that is related to the current level of difficulty (k) (i.e., no reference level of difficulty is involved in this scenario). Additionally, one specific variable attribute of each of the reference images 1202 is made to be different from the corresponding specific variable attribute of the visual element 1201, and the reference images 1202 may be identical to one another.

In the example of FIG. 12, a location of the center of the movable pattern for the visual element 1201 is different from a location of the center of the movable pattern for each of the reference images 1202.

In one embodiment, each of the questions includes a visual element that has a movable pattern and that is associated with the current level of difficulty, and the movable pattern has at least one visually conceivable attribute that is negatively related to the current level of difficulty. In one example, the movable pattern is a wave pattern, and the visually conceivable attribute is one of a wavelength and amplitude of the wave pattern.

To sum up, the embodiments of the disclosure provides a method for performing an assessment of vision. Various functions of vision may be assessed using one electronic device, which may be portable, to display questions of a wide variety. Additionally, by adjusting the current level of difficulty, the visual element and the reference image (s) presented to the user may be generated based on the user's ability to correctly answer the previous question (s), which may facilitate a more efficient and compact process of assessment.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for performing an assessment of vision to be implemented using an electronic device that includes a processor, an input unit and a display unit, the method comprising:
   a) determining, by the processor, a current level of difficulty for the assessment of vision;
   b) controlling, by the processor, the display unit to display a question of the assessment of vision, the question including at least one visual element that has a movable pattern, the movable pattern having at least one variable attribute that is related to the current level of difficulty;
   c) in response to receipt of an inputted answer via the input unit, determining, by the processor, whether the inputted answer is correct;
   d) determining, by the processor, based on the determination of step c), whether the assessment of vision is to be concluded; and
   e) when it is determined that the assessment of vision is to be concluded, generating, by the processor, a result of the assessment of vision based on the current level of difficulty,
   wherein the determination of step d) is done based on an applicable difficulty-adjustment rule for the assessment of vision and the inputted answer;
   wherein the at least one visual element has a movable pattern and is associated with the current level of difficulty, and the movable pattern has a wavelength that is negatively related to the current level of difficulty;
   wherein the at least one visual element includes a plurality of pixels, and in step b), the processor is programmed to generate each of the plurality of pixels based on a location of the pixel, a moving direction of the movable pattern, a time point, an average brightness and a maximum amplitude; and
   wherein the question includes only one visual element, and step b) includes controlling the display to display the question that includes the only one visual element, and an instruction to answer the question by identifying a location of a center of the movable pattern:
   wherein in generating the visual element with N*N pixels, the processor employs the following equation for each pixel at one of T number of time points that are evenly distributed in a specific period of movement of the movable pattern:

$$R2(i, j, p, q, t) = B + \left[A \cdot \sin\left(\frac{\pi k}{N}\sqrt{(i-p)^2 + (j-q)^2} - \frac{2\pi}{T}t\right)\right],$$

where $(i,j) \in \{0, 1, \ldots, N-1\}^2$ represents a location of the pixel of the visual element, $(p,q) \in \{0, 1, \ldots, N-1\}^2$ represents a location of a center of the movable pattern, $t \in \{0, 1, \ldots, T-1\}$ represents said one of the T number of time points, B represents an average brightness, A represents a maximum amplitude, k is the current level of difficulty, and R2 represents pixel value of the pixel located at (i, j).

2. The method of claim 1, further comprising, when it is determined that the assessment is not yet to be concluded:
   implementing step a) for determining the current level of difficulty;
   controlling, by the processor, the display unit to display another question of the assessment of vision based on the current level of difficulty; and
   repeating step c) and step d).

3. The method of claim 1, further comprising, prior to step a):
   g) determining, by the processor, the applicable difficulty-adjustment rule for the assessment of vision selected from one of a first difficulty-adjustment rule, a second difficulty-adjustment rule, a third difficulty-adjustment rule and a fourth difficulty-adjustment rule;
   wherein, when it is determined that the assessment is not yet to be concluded, step a) is implemented by:
   when the applicable difficulty-adjustment rule is the first difficulty-adjustment rule, adjusting the current level of difficulty by adding a first increment number;
   when the applicable difficulty-adjustment rule is the second difficulty-adjustment rule, keeping the current level of difficulty unchanged,
   when the applicable difficulty-adjustment rule is the third difficulty-adjustment rule, adjusting the current level of difficulty by subtracting a first decrement number; and
   when the applicable difficulty-adjustment rule is the fourth difficulty-adjustment rule, keeping the current level of difficulty unchanged.

4. The method of claim 3, further comprising, when it is determined that the assessment is not yet to be concluded:
   implementing step g) based on the determination of step c) and the applicable difficulty-adjustment rule;
   implementing step a) for determining the current level of difficulty;
   controlling, by the processor, the display unit to display another question of the assessment of vision based on the current level of difficulty; and
   repeating step c) and step d).

5. The method of claim 4, wherein in step g):
when the applicable difficulty-adjustment rule is the first difficulty-adjustment rule and it is determined in step c) that the inputted answer is correct, the processor maintains the applicable difficulty-adjustment rule as the first difficulty-adjustment rule;
when the applicable difficulty-adjustment rule is the first difficulty-adjustment rule and it is determined in step c) that the inputted answer is incorrect, the processor switches the applicable difficulty-adjustment rule to the second difficulty-adjustment rule;
when the applicable difficulty-adjustment rule is the second difficulty-adjustment rule and it is determined in step c) that the inputted answer is correct, the processor switches the applicable difficulty-adjustment rule to the first difficulty-adjustment rule;
when the applicable difficulty-adjustment rule is the second difficulty-adjustment rule and it is determined in step c) that the inputted answer is incorrect, the processor switches the applicable difficulty-adjustment rule to the third difficulty-adjustment rule;
when the applicable difficulty-adjustment rule is the third difficulty-adjustment rule and it is determined in step c) that the inputted answer is incorrect, the processor maintains the applicable difficulty-adjustment rule as the third difficulty-adjustment rule;
when the applicable difficulty-adjustment rule is the third difficulty-adjustment rule and it is determined in step c) that the inputted answer is correct, the processor switches the applicable difficulty-adjustment rule to the fourth difficulty-adjustment rule; and
when the applicable difficulty-adjustment rule is the fourth difficulty-adjustment rule and it is determined in step c) that the inputted answer is incorrect, the processor switches the applicable difficulty-adjustment rule to the third difficulty-adjustment rule.

6. The method of claim 5, wherein in step d), the processor determines that the assessment of vision is to be concluded when the applicable difficulty-adjustment rule is the fourth difficulty-adjustment rule, and it is determined in step c) that the inputted answer is correct.

7. The method of claim 3, wherein in step g), the applicable difficulty-adjustment rule is further selected from a fifth difficulty-adjustment rule and a sixth difficulty-adjustment rule;
when the applicable difficulty-adjustment rule is the fifth difficulty-adjustment rule and it is determined in step c) that the inputted answer is correct, the processor maintains the applicable difficulty-adjustment rule as the fifth difficulty-adjustment rule;
when the applicable difficulty-adjustment rule is the fifth difficulty-adjustment rule and it is determined in step c) that the inputted answer is incorrect, the processor switches the applicable difficulty-adjustment rule to the sixth difficulty-adjustment rule;
when the applicable difficulty-adjustment rule is the sixth difficulty-adjustment rule and it is determined in step c) that the inputted answer is correct, the processor switches the applicable difficulty-adjustment rule to the first difficulty-adjustment rule; and
when the applicable difficulty-adjustment rule is the sixth difficulty-adjustment rule and it is determined in step c) that the inputted answer is incorrect, the processor maintains the applicable difficulty-adjustment rule as the sixth difficulty-adjustment rule.

8. The method of claim 7, wherein, when it is determined that the assessment is not yet to be concluded, step a) is implemented by:
when the applicable difficulty-adjustment rule is the fifth difficulty-adjustment rule, adjusting the current level of difficulty by adding a second increment number that is larger than the first increment number; and
when the applicable difficulty-adjustment rule is the sixth difficulty-adjustment rule, adjusting the current level of difficulty by subtracting a second decrement number that is larger than the first decrement number.

9. A method for performing an assessment of vision to be implemented using an electronic device that includes a processor, an input unit and a display unit, the method comprising:
a) determining, by the processor, a current level of difficulty for the assessment of vision;
b) controlling, by the processor, the display unit to display a question of the assessment of vision, the question including at least one visual element that has a movable pattern, the movable pattern having at least one variable attribute that is related to the current level of difficulty;
c) in response to receipt of an inputted answer via the input unit, determining, by the processor, whether the inputted answer is correct;
d) determining, by the processor, based on the determination of step c), whether the assessment of vision is to be concluded; and
e) when it is determined that the assessment of vision is to be concluded, generating, by the processor, a result of the assessment of vision based on the current level of difficulty, wherein the determination of step d) is done based on an applicable difficulty-adjustment rule for the assessment of vision and the inputted answer;
wherein the movable pattern has at least one visually conceivable attribute that is negatively related to the current level of difficulty;
wherein the movable pattern is a wave-based movable grid pattern that includes a set of component waves, and the visually conceivable attribute is one of a wavelength and an amplitude of the set of component waves;
wherein the at least one visual element includes a plurality of pixels, and in step b), the processor is programmed to generate each of the plurality of pixels based on a location of the pixel, a moving direction of the movable pattern, a time point, an average brightness and a maximum amplitude;
wherein the question includes only one visual element, and step b) includes controlling the display to display the question that includes the only one visual element, and an instruction to answer the question by identifying a location of a center of the movable pattern;
wherein in generating the visual element with N*N pixels, the processor employs the following equation for each pixel at one of T number of time points that are evenly distributed in a specific period of movement of the movable pattern:

$$R2(i, j, p, q, t) = B + \left[ A \cdot \sin\left(\frac{\pi k}{N} \sqrt{(i-p)^2 + (j-q)^2} - \frac{2\pi}{T} t\right) \right]$$

where $(i,j) \in \{0, 1, \ldots, N-1\}^2$ represents a location of the pixel of the visual element, $(p,q) \in \{0, 1, \ldots, N-1\}^2$ represents a location of a center of the movable pattern, t∈{0, 1, . . . , T−1} represents said one of the T number of time points, B represents an an average brightness, A represents a maximum amplitude, k is the current level of difficulty, and R2 represents pixel value of the pixel located at (i, j).

10. The method of claim 9, further comprising, when it is determined that the assessment is not yet to be concluded:
   implementing step a) for determining the current level of difficulty:
   controlling, by the processor, the display unit to display another question of the assessment of vision based on the current level of difficulty; and
   repeating step c) and step d).

11. The method of claim 9, further comprising, prior to step a):
   g) determining, by the processor, the applicable difficulty-adjustment rule for the assessment of vision selected from one of a first difficulty-adjustment rule, a second difficulty-adjustment rule, a third difficulty-adjustment rule and a fourth difficulty-adjustment rule;
   wherein, when it is determined that the assessment is not yet to be concluded, step a) is implemented by:
   when the applicable difficulty-adjustment rule is the first difficulty-adjustment rule, adjusting the current level of difficulty by adding a first increment number;
   when the applicable difficulty-adjustment rule is the second difficulty-adjustment rule, keeping the current level of difficulty unchanged;
   when the applicable difficulty-adjustment rule is the third difficulty-adjustment rule, adjusting the current level of difficulty by subtracting a first decrement number; and
   when the applicable difficulty-adjustment rule is the fourth difficulty-adjustment rule, keeping the current level of difficulty unchanged.

\* \* \* \* \*